United States Patent
Wang et al.

(10) Patent No.: US 10,913,697 B2
(45) Date of Patent: Feb. 9, 2021

(54) PROCESS FOR REDUCING 3,3,3-TRIFLUOROPROPYNE IN 2,3,3,3-TETRAFLUOROPROPENE

(71) Applicant: Honeywell International Inc., Morris Plains, NJ (US)

(72) Inventors: Haiyou Wang, Amherst, NY (US); Hsueh Sung Tung, Getzville, NY (US); Willie Josue Perez, Hudson, OH (US); Yian Zhai, Williamsville, NY (US); Ralph John Borowski, Depew, NY (US); Fang Huang Tu, Amherst, NY (US); Lucas Peter Labuda, Amherst, NY (US); John L. Welch, Williamsville, NY (US)

(73) Assignee: Honeywell International Inc., Charlotte, NC (US)

( * ) Notice: Subject to any disclaimer, the term of this patent is extended or adjusted under 35 U.S.C. 154(b) by 0 days.

(21) Appl. No.: 16/346,739

(22) PCT Filed: Nov. 2, 2017

(86) PCT No.: PCT/US2017/059679
§ 371 (c)(1),
(2) Date: May 1, 2019

(87) PCT Pub. No.: WO2018/085512
PCT Pub. Date: May 11, 2018

(65) Prior Publication Data
US 2020/0055804 A1 Feb. 20, 2020

Related U.S. Application Data

(60) Provisional application No. 62/416,206, filed on Nov. 2, 2016.

(51) Int. Cl.
C07C 17/00 (2006.01)
*C07C 17/395* (2006.01)
*C07C 17/42* (2006.01)
*C07C 21/18* (2006.01)

(52) U.S. Cl.
CPC ............ *C07C 17/395* (2013.01); *C07C 17/42* (2013.01); *C07C 21/18* (2013.01)

(58) Field of Classification Search
CPC ............................. C07C 17/395; C07C 17/42
See application file for complete search history.

(56) References Cited

U.S. PATENT DOCUMENTS

| 2012/0222448 A1 | 9/2012 | Chaki et al. |
| 2013/0105296 A1 | 5/2013 | Chaki et al. |
| 2014/0275662 A1 | 9/2014 | Kopkalli et al. |
| 2015/0005536 A1 | 1/2015 | Wang et al. |

FOREIGN PATENT DOCUMENTS

WO 2014150889 A1 9/2014

OTHER PUBLICATIONS

International Search Report and Written Opinion issued in PCT/US2017/059679, dated May 15, 2018, 9 pages.

*Primary Examiner* — Sikarl A Witherspoon
(74) *Attorney, Agent, or Firm* — Faegre Drinker Biddle & Reath LLP

(57) ABSTRACT

The invention relates to a process for reducing the concentration of a fluorinated alkyne impurity, such as 3,3,3-trifluoropropyne (TFPY), in 2,3,3,3-tetrafluoropropene (HFO-1234yf) which comprises contacting such a mixture with a caustic material, such as sodium hydroxide (NaOH), under conditions effective to reduce the concentration of the fluorinated alkyne impurity, including in some practices reducing the concentration by at least about 50%.

20 Claims, 1 Drawing Sheet

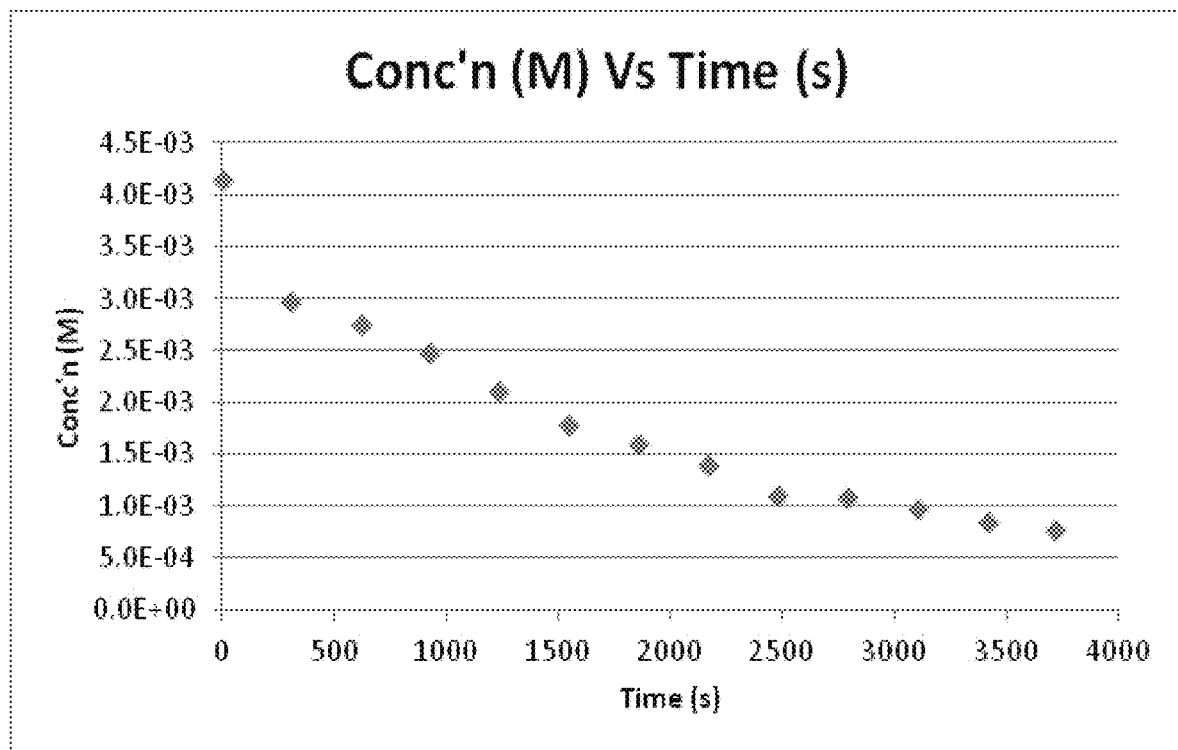

PROCESS FOR REDUCING 3,3,3-TRIFLUOROPROPYNE IN 2,3,3,3-TETRAFLUOROPROPENE

CROSS-REFERENCE TO RELATED APPLICATIONS

This application is a U.S. National Stage Application of International Application No. PCT/US2017/059679, filed Nov. 2, 2017, which claims priority to Provisional Application No. 62/416,206, filed Nov. 2, 2016, both of which are herein incorporated by reference in their entireties.

FIELD OF THE INVENTION

The invention provides a process for reducing fluorinated alkyne impurities in 2,3,3,3-tetrafluoropropene (HFO-1234yf) using a caustic material. In one embodiment, the level of TFPY (3,3,3-trifluoropropyne) impurity is reduced to levels of less than 100 ppm using a caustic such as sodium hydroxide (NaOH).

BACKGROUND OF THE INVENTION

Hydrofluoroolefins (HFOs), such as tetrafluoropropenes, including 2,3,3,3-tetrafluoropropene (HFO-1234yf), are known to be effective refrigerants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFOs pose no threat to the ozone layer. HFO-1234yf has also been shown to be a low global warming compound with low toxicity and, hence, can meet increasingly stringent requirements for refrigerants in mobile air conditioning. Accordingly, compositions containing HFO-1234yf are among the materials being developed for use in many of the aforementioned applications.

One manufacturing process for HFO-1234yf uses 1,1,2,3-tetrachloropropene (1230xa) as starting raw material. The process comprises the following three steps:

Step (1) 1230xa+3HF→2-chloro-3,3,3-trifluoropropene (1233xf)+3HCl in a vapor phase reactor charged with a solid catalyst;

Step (2) 1233xf+HF→2-chloro-1,1,1,2-tetrafluoropropane (244bb) in a liquid phase reactor charged with a liquid catalyst; and Step (3) 244bb→1234yf+HCl in a vapor phase reactor.

In Step (3), the final product—2,3,3,3-tetrafluoropropene (1234yf)—is commonly contaminated with fluorinated organic byproducts, such as fluorinated alkynes. These fluorinated alkynes include fluorinated propynes, such as 3,3,3-trifluoropropyne (TFPY). Due to the fact that both TFPY and 1234yf are light components having relatively low boiling points, using traditional purification methods, distillation, for example, will incur significant yield loss of 1234yf. TFPY is toxic and flammable; reducing the amount of TFPY in 1234yf using an improved method is therefore desirable.

SUMMARY OF THE INVENTION

In one embodiment, the invention is to a process for reducing the concentration of a fluorinated alkyne impurity in 2,3,3,3-tetrafluoropropene (HFO-1234yf); the process comprises contacting a mixture comprising 2,3,3,3-tetrafluoropropene (HFO-1234yf) and at least one fluorinated alkyne impurity having the formula RC≡CH wherein R is a perfluorinated straight chain $C_1$-$C_3$ alkyl with a caustic material under conditions effective to reduce the concentration of the alkyne impurity. The conditions effective include those whereby the caustic material forms a reaction product with at least some of the alkyne impurity, and whereby the HFO-1234yf remains substantially unreacted. By substantially unreacted, as used herein, it is meant that at least 90% HFO-1234yf by weight does not react with the caustic material. The reaction product can then be removed, reducing the concentration of the alkyne impurity from the HFO-1234yf. In one practice, the fluorinated alkyne impurity is TFPY. Caustic materials serviceable in the invention include, without limitation, alkali metal hydroxides, alkali metal oxides, alkali earth metal hydroxides, alkali earth metal oxides, and combinations thereof. In a preferred practice the caustic material is sodium hydroxide (NaOH). The concentration of the fluorinated alkyne impurity is reduced by at least about 20% (w/w); in another embodiment, the concentration of the fluorinated alkyne impurity is reduced by a least about 50% (w/w).

In a preferred embodiment, the invention is to a process for reducing the concentration of 3,3,3-trifluoropropyne (TFPY) in 2,3,3,3-tetrafluoropropene (HFO-1234yf) which comprises (a) providing a first composition comprising 2,3,3,3-tetrafluoropropene (HFO-1234yf) and a first concentration of 3,3,3-trifluoropropyne (TFPY); (b) contacting the first composition with a caustic material under conditions effective to react the caustic material with at least a portion of the TFPY; and (c) recovering a second composition comprising 1234yf and a second concentration of TFPY, the second concentration being less than the first concentration. In one practice, the first concentration of TFPY is greater than 300 parts per million by weight (ppm), and the second concentration of TFPY is 300 ppm or less. In other practices, the 200 ppm or less; preferably, 100 ppm or less.

BRIEF DESCRIPTION OF THE FIGURE

The FIGURE graphs the decrease in concentration of TFPY over time in an embodiment of the invention using 4% NaOH (w/w) as a caustic material at 25° C.

DETAILED DESCRIPTION OF THE INVENTION

The entire contents of U.S. Pat. No. 8,058,486 are incorporated herein. The operations described hereunder may be carried out in continuous, semi-continuous, or batch processes, or any combinations thereof.

In one embodiment, the invention provides a process for reducing the concentration of a fluorinated alkyne impurity in 2,3,3,3-tetrafluoropropene (HFO-1234yf) which comprises contacting a mixture comprising 2,3,3,3-tetrafluoropropene (HFO-1234yf) and at least one fluorinated alkyne impurity having the formula RC≡CH wherein R is a perfluorinated straight chain $C_1$-$C_3$ alkyl with a caustic material under conditions effective to reduce the concentration of the alkyne impurity. The conditions are such that a reaction product is formed between the caustic material and the alkyne impurity while the HFO-1234yf remains substantially unreacted and substantially intact. The reaction product can be removed to further isolate HFO-1234yf of increased purity. The term "reaction product" includes, without limitation, single and multiple products formed by contact of a caustic with an alkyne impurity as described herein, including without limitation, the decomposition or other product or products formed by contact of caustics such as NaOH with alkynes such as TFPY. The term "straight chain perfluorinated alkyl group", as used herein, means a straight-chain alkyl group wherein all hydrogens on carbon atoms of the alkyl group have been substituted by fluorines. Examples of a straight-chain perfluorinated alkyl group include —$CF_3$, —$CF_2CF_3$ and —$CF_2CF_2CF_3$. In a preferred practice, the perfluorinated alkyl group is —$CF_3$, i.e. the fluorinated alkyne impurity is 3,3,3-trifluoropropyne (TFPY).

Without limitation, in one practice, the starting concentration of fluorinated alkyne impurity in the mixture is greater than about 400 ppm, although the other starting concentrations, including concentrations lower than 400 ppm, are contemplated. Contacting can be accomplished by ways known in the art, including e.g. direct addition of the caustic material to composition comprised of HFO-1234yf and the fluorinated alkyne impurity; other methods of contacting include passing the composition comprising HFO-1234yf and the fluorinated alkyne impurity in vapor form through a reaction vessel or reactor charged with the caustic material. The HFO-1234yf having the reduced concentration of fluorinated alkyne impurity can be recovered by conventional methods, e.g. phase separation when the caustic material is directly added into the composition comprising HFO-1234yf and the fluorinated alkyne impurity; and compressing or using condensation when the composition comprised of HFO-1234yf and the fluorinated alkyne impurity is passed through the caustic material as a mixed vapor. Optionally, other purification means such as distillation can then be applied to further increase the purity of HFO-1234yf.

The caustic material may comprise, for example, alkali metal hydroxides, alkali metal oxides, alkali earth metal hydroxides, alkali earth metal oxides, and combinations thereof. Without limitation, examples of suitable alkali metal hydroxides include potassium hydroxide (KOH), sodium hydroxide (NaOH), lithium hydroxide (LiOH), cesium hydroxide (CsOH), rubidium hydroxide (RbOH), and combinations thereof. Non-limiting examples of alkali earth metal hydroxides include magnesium hydroxide ($Mg(OH)_2$), calcium hydroxide ($Ca(OH)_2$), strontium hydroxide ($Sr(OH)_2$), barium hydroxide ($Ba(OH)_2$), and combinations thereof. A representative, non-limiting example of an alkali earth metal oxide is calcium oxide (CaO). In a preferred embodiment, the caustic material is NaOH.

In one practice, the conditions effective include, without limitation, the caustic material being present in an aqueous solution at less than 50% by weight; in an embodiment, the caustic material is present in an aqueous solution at between 0.1% to about 20% by weight; in another embodiment, the caustic material is present in an aqueous solution at between about 1% to about 10% by weight; in a further embodiment, the caustic material is present in an aqueous solution at between about 2% to about 5% by weight; yet more preferably, the caustic material is present in an aqueous solution at between about 4% by weight. Without limitation, suitable temperatures for the contacting step include temperatures between about 0° C. and about 100° C.; in an embodiment between about 10° C. and about 80° C.; in a further embodiment between about 20° C. and about 60° C. Without limitation, suitable pressures for the contacting step include pressures between about 0.1 psig and about 1000 psig; in another embodiment between about 5 psig and about 500 psig; in a further embodiment between about 10 psig and about 100 psig. In one practice, the reaction product between the caustic material and the alkyne impurity can be removed from the HFO-1234yf by techniques known in the art, such as by phase separation, optionally followed by distillation.

In one embodiment, the practice of the invention reduces the concentration of the fluorinated alkyne impurity in the mixture by at least about 20%; preferably, the concentration of the fluorinated alkyne impurity in the mixture is reduced by at least about 30%; more preferably, the concentration of the fluorinated alkyne impurity in the mixture is reduced by at least about 40%; still more preferably, the concentration of the fluorinated alkyne impurity in the mixture is reduced by at least about 50%.

In another embodiment, the practice of the invention reduces the concentration of the fluorinated alkyne impurity to a level of about 300 ppm or less; in an embodiment, the concentration of the fluorinated alkyne impurity is reduced to a level of about 200 ppm or less; still, in another embodiment, the concentration of the fluorinated alkyne impurity is reduced to a level of about 100 ppm or less.

In another embodiment, the invention relates to a process for reducing the concentration of 3,3,3-trifluoropropyne (TFPY) in a composition comprised of same and 2,3,3,3-tetrafluoropropene (HFO-1234yf) which comprises (a) providing a first composition comprising 2,3,3,3-tetrafluoropropene (HFO-1234yf) and a first concentration of an fluorinated alkyne impurity such as 3,3,3-trifluoropropyne (TFPY); without limitation, the first concentration of TFPY, as representative of a fluorinated alkyne impurity, is greater than 300 ppm, although lower concentrations are contemplated. The process further includes (b) contacting the first composition with a caustic material under conditions effective to react the caustic material with at least a portion of the TFPY; the caustic materials are as described hereinabove including being provided in the form of an aqueous solution at the weight percentages described hereunder. In one practice, the caustic material comprises NaOH. In another embodiment, the NaOH is provided as aqueous solution of about 0.1% to about 20% NaOH by weight; in still another embodiment, the NaOH is provided as aqueous solution of about 1% to about 10% NaOH by weight; in another further embodiment, the NaOH is provided as aqueous solution of about 2% to about 5% NaOH by weight; still in another embodiment, the NaOH is provided as aqueous solution of about 4% NaOH by weight. The process further includes (c) recovering a second composition comprising 1234yf and a second concentration of TFPY, the second concentration being less than the first concentration; without limitation, in practices where the first concentration of TFPY is greater than 300 ppm, the second concentration of TFPY is 300 ppm or less; preferably, about 200 ppm or less; more preferably, about 100 ppm or less.

The process of the invention may be employed, for example, as part of a larger process to make compounds such as 2,3,3,3-tetrafluoropropene (1234yf). For example, the process of the invention can be related to Step (3) for the three-step process to make 1234yf as described above. In a preferred embodiment in this regard, for Step (3): the HCFC-244bb produced in Step (2) is dehydrohalogenated under conditions effective to produce 2,3,3,3-tetrafluoropropene (HFO-1234yf). Preferably the dehydrohalogenating step comprises a gas or vapor phase catalytic reaction. The catalytic conversion of HCFC-244bb is conducted under conditions effective to dehydrochlorinate HCFC-244bb to produce 2,3,3,3-tetrafluoropropene (HFO-1234yf). Preferably dehydrochlorination of HCFC-244bb is done in a vapor phase, and more preferably in a fixed-bed reactor in the vapor phase. The dehydrohalogenation reaction may be conducted in any suitable reaction vessel or reactor, but it should preferably be constructed from materials which are resistant to the corrosive effects of hydrogen chloride (to the extent that such material is formed under the dehydrohalogenation conditions) such as nickel and its alloys, including Hastelloy, Inconel, Incoloy, and Monel or vessels lined with fluoropolymers and may employ single or multiple tubes packed with a dehydrohalogenation catalyst.

The catalysts can include metal halides, halogenated metal oxides, neutral (or zero oxidation state) metal or metal alloy, or activated carbon in bulk or supported form. When metal halides or metal oxides catalysts are used, preferably mono-, bi-, and tri-valent metal halides, oxide and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $C_{1-2}$, HBr, $Br_2$, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625.

HCFC-244bb can be introduced into the reactor either in pure form, partially purified form, or as part of the reactor effluent from the preceding step. The HCFC-244bb may optionally be fed with an inert gas diluent such as nitrogen, argon, or the like. In an embodiment of the invention, the HCFC-244bb is pre-vaporized or preheated prior to entering the reactor. Alternately, the HCFC-244bb is vaporized inside the reactor. Useful reaction temperatures may range from about 100° C. to about 700° C. Preferred temperatures may range from about 150° C. to about 600° C., and more preferred temperatures may range from about 200° C. to about 550° C. The reaction may be conducted at atmospheric pressure, super-atmospheric pressure or under vacuum. The vacuum pressure can be from about 5 torr (0.0966 psia) to about 760 torr (14.69 psia). Contact time of the HCFC-244bb with the catalyst may range from about 0.5 seconds to about 120 seconds, however, longer or shorter times can be used.

In such dehydrofluorination embodiments as herein described, the conversion of the HCFC-244bb is at least about 10%, more preferably at least about 20%, and even more preferably at least about 30%. Preferably in such embodiments, the selectivity to HFO-1234yf, is at least about 70%, more preferably at least about 85% and more preferably at least about 95%.

In an embodiment, the process flow may be in the down or up direction through a bed of the catalyst or horizontal direction. It may also be advantageous to periodically regenerate the catalyst after prolonged use while in place in the reactor. Regeneration of the catalyst may be accomplished by any means known in the art such as using an oxidizing agent such as $O_2$ or chlorine. For example, the catalyst may be regenerated by passing air or air diluted with nitrogen over the catalyst at temperatures of from about 100° C. to about 400° C., and in another embodiment from about 200° C. to about 375° C., for from about 0.5 hour to about 3 days depending on the size of the reactor. The regeneration of the catalyst may also involve the use of a reducing agent such as $H_2$. Other reducing agents include, without limitation, $NH_3$ (ammonia), CO (carbon monoxide), $CH_4$ (methane); mixtures of these, including mixtures with hydrogen, may also be used.

In general, the effluent from the dehydrohalogenation reaction step, including any intermediate effluents that may be present in multi-stage reactor arrangements, may be processed to achieve desired degrees of separation and/or other processing. For example, in embodiments in which the reactor effluent comprises HFO-1234yf, the effluent will generally also include HCl and unreacted HCFC-244bb. Some portion or substantially all of these components of the reaction product may be recovered via any separation or purification method known in the art such as neutralization and distillation. The concentration of alkyne impurities, such as TFPY, can be reduced by the practice of the present invention. It is expected that unreacted HCFC-244bb can be recycled, completely or partially, to improve the overall yield of the desired $CF_3CF=CH_2$ (HFO-1234yf). Optionally, hydrogen chloride is then recovered from the result of the dehydrochlorination reaction. Recovering of hydrogen chloride is conducted by conventional distillation where it is removed from the distillate.

Alternatively, HCl can be recovered or removed by using water or caustic scrubbers. When a water extractor is used HCl is removed as an aqueous solution. When caustic is used, HCl is just removed from system as a chloride salt in aqueous solution.

In an alternate embodiment of the invention, dehydrohalogenation of HCFC-244bb can also be accomplished by reacting it with a strong caustic solution that includes, but is not limited to KOH, NaOH, $Ca(OH)_2$ and CaO at an elevated temperature. This is described in US Patent Publication No. 2011/0270000. In this case, the strength of the caustic solution is from about 2 wt % to about 100 wt %, in another embodiment from about 5 wt % to about 90 wt % and still in a further embodiment from about 10 wt % to about 80 wt %. The caustic to HCFC-244bb mole ratio preferably ranges from about 1:1 to about 2:1; more preferably from about 1.1:1 to about 1.5:1 and most preferably from about 1.2:1 to about 1.4:1. The reaction may be conducted at a temperature of from about 20° C. to about 100° C., in another embodiment from about 30° C. to about 90° C. and in a further embodiment from about 40° C. to about 80° C. As above, the reaction may be conducted at atmospheric pressure, super-atmospheric pressure or under vacuum. The vacuum pressure can be from about 5 torr (14.80 psig) to about 760 torr (29.40 psig). In addition, a solvent or phase transfer catalyst such as Aliquat 336 may optionally be used to help dissolve the organic compounds in the caustic solution. This optional step may be conducted using solvents that are well known in the art for said purpose. Thereafter, HFO-1234yf may be recovered from the reaction product mixture comprised of unreacted starting materials and by-products by any means known in the art, such as by extraction and preferably distillation. The mixture of HFO-1234yf and any by-products are passed through a distillation column. For example, the distillation may be preferably conducted in a standard distillation column at atmospheric pressure, super-atmospheric pressure or a vacuum. Preferably the pressure is less than about 300 psig, preferably less than about 200 psig and most preferably less than 150 psig. The pressure of the distillation column inherently determines the distillation operating temperature. Preferably in such dehydrofluorination embodiments as described in this section, the conversion HCFC-244bb is at least about 60%, mote preferably at least about 75%, and even more preferably at least about 90%. Preferably in such embodiments, the selectivity to HFO-1234yf, is at least about 70%, more preferably at least about 85% and more preferably at least about 95%

Unless indicated to the contrary, all percentages and ppm are weight-based.

In addition, as used herein, the term "caustic" and "caustic material" are synonymous and are used interchangeably.

The following non-limiting examples serve to illustrate the invention.

EXAMPLES

The foregoing description is by way of example only and is not limiting to the scope of the invention.

Example 1

A TFA (trifluoroacetic acid)/D$_2$O insert was placed inside an NMR tube. About 1.0 g of DI water was added sufficient to just cover the insert. The exact weight of DI water was recorded. The NMR tube was then equilibrated in a temperature bath at 25° C. for about 2 minutes. After that, a pure sample of 3,3,3-trifluoropropyne (TFPY) gas was slowly bubbled into the liquid using a fine peek tube to saturate the water and to saturate the headspace above the water. The NMR tube was immediately capped tightly to prevent any escape of the gas. The initial concentration of TFPY (at time, t=0) was determined by $^{19}$F NMR analysis at 25° C. The concentration of the dissolved gas was calculated against a calibrated TFA/D$_2$O insert. Next, a sample of 44% NaOH solution was prepared and about 0.1 g sample was injected into the sample and mixed. This made about 4% NaOH by weight solution. The time of injection was noted and the sample was analyzed by $^{19}$F NMR every 5-6 minutes for 1 hour. The concentration of TFPY in 4% NaOH (w/w) solution was measured and plotted and is shown in the FIGURE. The FIGURE graphically depicts the TFPY concentration in 4% NaOH solution as a function of time at 25° C. As shown in the FIGURE, the concentration of 3,3,3-trifluoropropyne decreased with time, indicating the occurrence of reaction between TFPY and NaOH.

Comparative Example 1

Instead of 3,3,3-trifluoropropyne, 2,3,3,3-tetrafluoropropene (HFO-1234yf) was used in Comparative Example 1. Following the same procedure as described in Example 1, it was found the concentration of HFO-1234yf in 4% NaOH (w/w) solution remained constant, indicating no reaction occurs between HFO-1234yf and NaOH.

Example 2

A 1 L Tedlar gas was filled with 3,3,3-trifluoropropyne (TFPY) gas at room temperature, and a 2.11 g 4% NaOH solution was injected into the bag through septum. The liquid was allowed to react for 4 days with occasional swirling of the bag. The liquid was carefully drawn out of the bag with a syringe and analyzed by $^{19}$F NMR with calibrated TFA (trifluoroacetic acid)/D$_2$O insert. The results showed the peak at −51.0 ppm (which was attributed to TFPY) decreased while the peak at −119.9 ppm (which was attributed to F$^-$) increased as the reaction proceeded, indicating part of TFPY was reacted away and fluoride was formed as one of reaction products. The integration also showed that the conversion from TFPY to fluoride ion was quantitative. By extending the reaction time to 6 days after the liquid was injected back to the bag to ensure the completion of the reaction, the TFPY reaction capacity in 4% NaOH (w/w) solution was determined to be about 1.7% to 1.8% (w/w) of the amount of 4% NaOH (w/w) solution.

Example 3

A 750 g mixture of 1234yf and TFPY (0.5% TFPY) is passed through a 200 ml 4% NaOH (w/w) aqueous solution at room temperature and 1 atm pressure via a gas sparger, and the tail gas is collected in liquid nitrogen trap. The collected material was analyzed by GC and GCMS. The results show the concentration of TFPY in 1234yf is reduced to about 260 ppm, and the recovery of 1234yf was 99%.

In another experiment, the same procedure was used except for using 4% (w/w) KOH aqueous solution, similar results are obtained.

Example 4

A 750 g mixture of 1234yf and TFPY (0.5% TFPY) was passed through a 210 ml 4% w/w NaOH aqueous solution at room temperature and 1 atm pressure via a gas sparger, and the tail gas was collected in liquid nitrogen trap. The collected material was analyzed by GC and GCMS. The results show the concentration of TFPY in 1234yf was reduced to about 20 ppm w/w, and the recovery of 1234yf is 99%.

In another experiment, the same procedure was used except for using 4% w/w KOH aqueous solution, similar results are obtained.

Example 5

A 175 g mixture of 1234yf and TFPY (0.5% w/w TFPY) was passed through a 200 ml % (w/w) NaOH aqueous solution at room temperature and 1 atm pressure via a gas sparger, and the tail gas was collected in liquid nitrogen trap. The collected material was analyzed by GC and GCMS. The results show the concentration of TFPY in 1234yf was reduced to about 75 ppm w/w, and the recovery of 1234yf was 99%.

In another experiment, the same procedure was used except for using 1% (w/w) KOH aqueous solution, similar results are obtained.

Example 6

A 2000 g mixture of 1234yf and TFPY (0.5% w/w TFP) was passed through a 205 ml 10% w/w NaOH aqueous solution at room temperature via a gas sparger, and the tail gas is collected in liquid nitrogen trap. The collected material was analyzed by GC and GCMS. The results show the concentration of TFPY in 1234yf was reduced to 165 ppm w/w, and the recovery of 1234yf was 98%.

In another experiment, the same procedure was used except for using 10% w/w KOH aqueous solution, similar results were obtained.

What is claimed is:

1. A process for producing purified 2,3,3,3-tetrafluoropropene, the process comprising reducing the concentration of a fluorinated alkyne impurity in 2,3,3,3-tetrafluoropropene (HFO-1234yf) by contacting a mixture comprising HFO-1234yf and at least one fluorinated alkyne impurity having the formula RC≡CH, wherein R is a perfluorinated straight chain $C_1$-$C_3$ alkyl, with a caustic material under conditions effective whereby at least one reaction product between the caustic material and at least a portion of the alkyne impurity is formed, and whereby the HFO-1234yf remains substantially unreacted.

2. The process of claim 1 further comprising recovering the HFO-1234yf having the reduced concentration of said fluorinated alkyne impurity.

3. The process of claim 1 wherein R is —$CF_3$.

4. The process of claim 1 wherein the caustic material is selected from the group consisting of an alkali metal hydroxide, an alkali metal oxide, an alkali earth metal hydroxide, an alkali earth metal oxide, and combinations thereof.

5. The process of claim 4 wherein the alkali metal hydroxide is selected from the group consisting of potassium hydroxide (KOH), sodium hydroxide (NaOH), lithium hydroxide (LiOH), cesium hydroxide (CsOH), rubidium hydroxide (RbOH), and combinations thereof.

6. The process of claim 4 wherein the alkali earth metal hydroxide is selected from the group consisting of magnesium hydroxide ($Mg(OH)_2$), calcium hydroxide ($Ca(OH)_2$), strontium hydroxide ($Sr(OH)_2$), barium hydroxide ($Ba(OH)_2$), and combinations thereof.

7. The process of claim 4 wherein the alkali earth metal oxide is calcium oxide (CaO).

8. The process of claim 1 wherein the caustic material is present in an aqueous solution at less than about 50% by weight of the caustic material.

9. The process of claim 8 wherein the caustic material is present in an aqueous solution at between about 0.1% to about 20% by weight of the caustic material.

10. The process of claim 9 wherein the caustic material is present in an aqueous solution at between about 2% to about 5% by weight of the caustic material.

11. The process of claim 10 wherein the caustic material is NaOH.

12. The process of claim 1 wherein the concentration of the fluorinated alkyne impurity is reduced by at least about 20%.

13. The process of claim 12 wherein the concentration of the fluorinated alkyne impurity is reduced by at least about 50%.

14. A process for reducing the concentration of 3,3,3-trifluoropropyne (TFPY) in 2,3,3,3-tetrafluoropropene (HFO-1234yf) which comprises:
   (a) providing a first composition comprising 2,3,3,3-tetrafluoropropene (HFO-1234yf) and a first concentration of 3,3,3-trifluoropropyne (TFPY);
   (b) contacting the first composition with a caustic material under conditions effective to react the caustic material with at least a portion of the TFPY; and
   (c) recovering a second composition comprising 1234yf and a second concentration of TFPY, the second concentration being less than the first concentration.

15. The process of claim 14 wherein first concentration of TFPY is greater than 300 ppm.

16. The process of claim 14 wherein the second concentration of TFPY is 300 ppm or less.

17. The process of claim 16 wherein the second concentration of TFPY is about 100 ppm or less.

18. The process of claim 14 wherein the caustic material comprises NaOH.

19. The process of claim 18 wherein the NaOH is provided as aqueous solution of about 0.1% to about 20% NaOH by weight.

20. The process of claim 19 wherein the NaOH is provided as aqueous solution of about 4% NaOH by weight.

* * * * *